Figure 1:
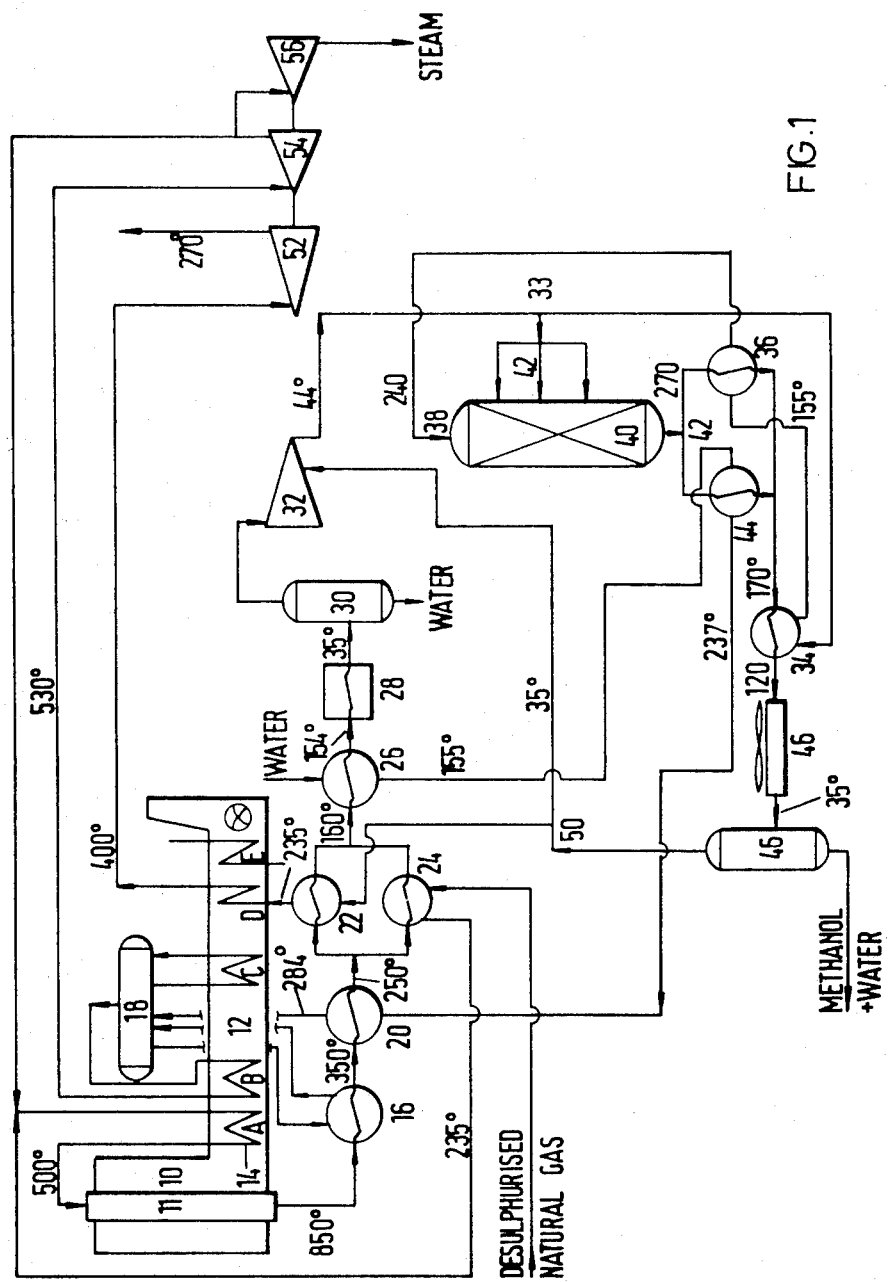

United States Patent [19]

Pinto

[11] 4,065,483
[45] Dec. 27, 1977

[54] METHANOL

[75] Inventor: Alwyn Pinto, Stockton-on-Tees, England

[73] Assignee: Imperial Chemical Industries Limited, London, England

[21] Appl. No.: 590,012

[22] Filed: June 24, 1975

[30] Foreign Application Priority Data

July 2, 1974 United Kingdom ............... 29260/74

[51] Int. Cl.$^2$ ..................... C07C 29/16; C07C 31/06
[52] U.S. Cl. ................................................. 260/449.5
[58] Field of Search ..................................... 260/449.5

[56] References Cited

U.S. PATENT DOCUMENTS

| | | |
|---|---|---|
| 2,632,528 | 3/1953 | Berg et al. .................... 260/449.5 X |
| 2,662,911 | 12/1953 | Dorschner et al. ........ 260/449.5 UX |
| 3,254,967 | 6/1966 | Wentworth .................. 260/449.5 X |
| 3,441,393 | 4/1969 | Finneran et al. ..................... 218/197 |
| 3,501,516 | 3/1970 | Parrish ............................. 260/449.5 |
| 3,531,266 | 4/1970 | Chernoff ...................... 260/449.5 X |
| 3,598,527 | 8/1971 | Quartulli et al. ............. 260/449.5 X |
| 3,615,200 | 10/1971 | Konoki ........................... 260/449.5 X |
| 3,694,169 | 9/1972 | Fawcett et al. ............... 260/449.5 X |
| 3,920,717 | 11/1975 | Marion ............................. 260/449.5 |

FOREIGN PATENT DOCUMENTS

| | | |
|---|---|---|
| 7,015,447 | 4/1971 | Netherlands ...................... 260/449.5 |
| 1,309,872 | 3/1973 | United Kingdom ............. 260/449.5 |
| 1,316,705 | 5/1973 | United Kingdom ............. 260/449.5 |
| 1,272,798 | 5/1972 | United Kingdom ............. 260/449.5 |

OTHER PUBLICATIONS

Melta, Hydrocarbon Processing, May 1976, 165–168.

*Primary Examiner*—Howard T. Mars
*Attorney, Agent, or Firm*—Cushman, Darby & Cushman

[57] ABSTRACT

In a process for producing methanol by generating methanol synthesis gas, generating high pressure steam by heat exchange with a hot gaseous stream produced in the course of synthesis gas generation, bringing synthesis gas to synthesis gas pressure by means of a compressor powered from an engine in which such high pressure steam is let down, and synthesising methanol over a catalyst at an outlet temperature of under 300° C, thermal efficiency is improved by transferring heat evolved in the synthesis to water maintained under a pressure too high to permit boiling and the resulting hot water is used as feed for the high pressure steam generation. If the methanol synthesis is of the recirculatory type and involves a purge, the purge gas is heated and let down in pressure in an expansion engine.

12 Claims, 2 Drawing Figures

METHANOL

This invention relates to a process for producing methanol by the catalytic reaction of one or more carbon oxides with hydrogen.

The reaction of carbon oxides with hydrogen to give methanol is exothermic.

$$CO + 2H_2 \rightarrow CH_3OH \quad \Delta H = -21685 \text{ kg cal/mol}$$

$$CO_2 + 3H_2 \rightarrow CH_3OH + H_2O \quad \Delta H = -11830 \text{ kg cal/mol}$$

and therefore in principle a methanol synthesis process should be capable of providing a quantity of usable heat. In modern methanol synthesis processes using a copper-containing catalyst, however, the highest temperature obtained by the reacting mixture of carbon oxides and hydrogen is usually under 300° C and rarely above 270° C. Consequently it is not practicable by passing such mixture through a waste-heat boiler to raise steam at a pressure greater than about 50 ata. Steam at such a relatively low pressure can, of course, be made use of; and, indeed, processes have been proposed in which steam is raised in a special reactor in which the catalyst is disposed in the tubes of a boiler or boiler tubes are disposed between layers of catalyst. The disadvantages enter in, however, that turbines in which such steam can be let down for power recovery are thermodynamically limited in efficiency as compared with higher-pressure turbines. Turbines of the condensation type may be used but these are higher in capital cost than the pass-out turbines employed when higher-pressure steam is generated, as in many ammonia plants. Moreover the special catalytic reactors are complicated and expensive.

A methanol production plant normally includes, in addition to the synthesis section, a synthesis gas generation section in which a carbonaceous feedstock is converted to carbon oxides and hydrogen by a high temperature reaction with steam and/or oxygen. We have realised that by integrating in a special way the heat recovery in the synthesis gas generation section a highly efficient over-all heat recovery can be obtained with less incidence of the abovementioned disadvantages.

According to the first aspect of the invention there is provided a methanol production process which comprises a. generating methanol synthesis gas in one or more stages in at least one of which there is produced a gas stream at over 400° C;
b. generating steam at a pressure of at least 50 ata, by heat exchange with such stream or streams;
c. bringing synthesis gas to synthesis pressure by means of a compressor powered from an engine in which such steam is let down;
d. synthesising methanol over a catalyst at an outlet temperature of under 300° C;
e. transferring heat evolved in the synthesis of stage (d) from methanol-containing synthesis gas to water to heat the water to a temperature in the range 200° C to 260° C, the water maintained under a pressure too high to permit boiling to take place;
f. passing the resulting hot water to stage (b) as feed for the steam generation; and
g. recovering methanol from the cooled gas from stage (e).

Methanol synthesis gas generation usually involves the reaction of a carbonaceous feedstock, such as natural gas, refinery off-gas, gaseous hydrocarbons, non-vaporisable hydrocarbons, coal or coke, with steam and possibly also carbon dioxide or oxygen. The reaction of such materials takes place typically at over 700° C and may be as high as 1100° C for a catalytic process, still higher for a non-catalytic process, in order to effect sufficiently complete reaction to crude synthesis gas containing carbon oxides and hydrogen. If the feedstock is one of the first 4 mentioned the reaction is most often carried out without oxygen over a catalyst in tubes externally heated in a furnace ("steam reforming") but can be carried out in an insulated vessel if oxygen is also fed ("partial oxidation"). If the feedstock is one of the last 4, the reaction is usually carried out in the presence of oxygen without a catalyst. Depending on the hydrogen-to-carbon-ratio of the carbonaceous feedstock and on the extent to which oxygen is used, synthesis gas generation may involve a CO-shift and $CO_2$-removal stage to bring the hydrogen to carbon oxides ratio to the level required for methanol synthesis. The crude synthesis gas is cooled and freed from its content of unreacted steam before passing it to the synthesis section.

Synthesis gas generation may alternatively begin with the shift reaction of carbon monoxide with steam to give carbon dioxide and hydrogen (outlet temperature over 400° C) and $CO_2$-removal, if carbon monoxide is available as a starting material.

The pressure in the synthesis gas generation section is typically up to 100 ata and thus the gas usually has to be compressed before feeding it to the methanol synthesis.

The streams by heat exchange with which steam is generated in stage (b) include the crude synthesis gas stream and the flue gas of the furnace if a steam reforming process is used. The steam pressure is preferably in the range 80-120 ata, as a result of which it is practicable to let it down in an engine of the pass-out type and to use the exhaust steam as the feed for the synthesis gas generation section. The engine may drive the synthesis gas compressor directly or may drive an electric generator powering the compressor. In favourable conditions enough steam can be generated to provide, directly or indirectly, the mechanical power required in other parts of the process, such as the synthesis gas circulator (if a recycle process is used) and various feed-pumps and fans. It is within the invention, however, to raise some of the steam in a fired boiler or by burning fuel in the flue-gas duct of a reformer furnace, and to use some of the waste-heat steam in condensing engines or in engines exhausting at less than synthesis gas generation pressure, for example into the re-boiler of a methanol distillation.

After the waste-heat boiler and the economiser associated with it for the steam generation, the temperature of the streams of crude synthesis gas or reformer furnace flue gas is suitably in the range 200°–300° C and preferably more than 225° C. This can be higher than is typical of methanol processes previously proposed because the water fed to the economiser has been heated (for example to 200°–260° C) by heat evolved in the synthesis instead of merely being warmed (for example to 140°–180° C) by further heat exchange with crude synthesis gas. As a result, other streams can be heated by the crude synthesis gas, in particular the hydrocarbon feed to the synthesis gas generation section and/or purge gas from the synthesis, especially if it is to be let-down in an engine according to the second aspect of the invention described below. A further result of water-heating by heat evolved in the synthesis is that the temperature differences across the boiler and economiser can be smaller than were previously used, and thus they can be smaller units. Thus the capital cost of the added heat exchangers is in part repaid by the lower cost of the boiler and economiser.

After heating the other streams the crude synthesis gas or reformer furnace flue gas is typically at 140°–180° C and can warm the boiler feed water to be heated by heat evolved in the synthesis and can raise low pressure steam before being cooled below the dew-point of the steam contained in it.

The methanol synthesis at under 300° C can be at any convenient pressure. Recently developed processes at 50 ata or 100 ata are very suitable as part of the process of the invention, but lower and higher pressures, for example in the range 30–400 ata can be used. The catalyst for such processes usually contains copper and also zinc oxide and one or more further oxides, such as chromium oxide, as described for example in our UK specification 1,010,871 or oxides from Groups II-IV of the Periodic Table (especially of aluminium) as described for example in our UK Specification 1,159,035, or possibly of manganese or vanadium.

A variety of general types of methanol synthesis process have been proposed, differing in the methods adopted for handling the heat evolved in the synthesis reaction. Any one or more of these can be used excepting, of course, those designed to use directly all the relatively low pressure ("intermediate pressure") steam generated by heat exchange with the reacting gas or reacted gas in the synthesis. Thus synthesis may be over a catalyst in tubes surrounded by a coolant or in the space around tubes containing coolant. The coolant may be for example pressurised water or a mixture of diphenyl and diphenyl ether; the pressurised water can be used as feed for the high pressure steam generation or, like the mixture, heat-exchanged in liquid form with boiler feed water to be fed to the high pressure steam generation. Alternatively the coolant water may be allowed to boil and the resulting intermediate pressure steam condensed in heat exchange with water maintained under a pressure too high to permit boiling to take place at a temperature in the range 200° C to 260° C, and the resulting hot water to be fed to the high pressure steam generation. In another process the catalyst bed can be in several parts with heat-abstraction by coolant between the parts. In a third process the catalyst temperature can be controlled by heat exchange with cool feed gas passing through tubes in the catalyst bed or through the space surrounding catalyst-filled tubes. For the first two of such processes reactors not much simpler than previously proposed steam-raising processes are required, however, and it may therefore be preferred to use the third or, better still, a process in which the temperature is controlled by injecting cool synthesis gas ("quench gas") into the hot reacting synthesis gas. Quench gas can be injected into mixing chambers between successive parts of a catalyst bed or successive reactor vessels. A very convenient system involves a single body of catalyst in which are disposed catalyst-free perforated hollow bars each having a sparger for introducing the quench gas, the bars being large enough in cross section for their interiors to constitute mixing zones and close enough together or to the catalyst bed walls to cause a substantial proportion of reaction mixture to pass through their interiors, as described in our UK specification 1,105,614. The temperature of quench gas can be below 50° C, but thermal efficiency is better if it is at between 50° and 150° C, as will be discussed below.

The volume space velocity of the flow of gas through the catalyst bed is typically in the range 5000–50000 hour$^{-1}$ and is preferably fixed at a level such that the gas leaves the catalyst bed when the quantity of methanol formed has been sufficient to raise the gas temperature to the design level, which is under 300° C and most preferably under 270° C. The methanol content of the reacted gas is for example 2–5% for a process at 50 ata and proportionately more at higher pressures. Consequently unreacted carbon oxides and hydrogen are left over after methanol has been recovered and are preferably passed again over a methanol synthesis catalyst, for example, by recirculation to the inlet of the catalyst and mixing with fresh synthesis gas. The above space velocity range refers to the mixture in such a process.

In a preferred way of transferring to the feed water for high pressure steam generation the heat evolved in the synthesis, reacted gas leaving the catalyst is passed through two parallel heat exchanges, the first of which heats synthesis gas to synthesis inlet temperature, which is preferably 20°–40° C lower than the outlet temperature of the catalyst bed. The second heats water to a temperature preferably in the range 200°–260° C under a pressure too high to permit boiling to take place or heats a coolant (such as described above) from which heat is to be transferred to such water. The reacted gas becomes cooled initially to 150°–190° C in these exchangers. Preferably it is then (suitably after re-uniting the two streams) heat-exchanged with cold synthesis gas from the generation section or methanol recovery or both. This affords a useful secondary heat recovery and decreases the capacity required of the first heat exchanger. After secondary heat recovery the gas is passed to a cooler and separator for recovery of methanol.

In the alternative way of tranferring heat to the feed water, by raising steam in the reactor and condensing it in heat exchange with the feed water, the reacted gas leaving the reactor can be cooled to 50°–150° C in a single heat exchange with cold synthesis gas and then passed to the cooler and separator.

Unreacted gas from the separator is preferably recirculated but, if the fresh synthesis gas has a hydrogen to carbon oxides ratio different from stoichiometric and/or contains non-reactive gases such as nitrogen, methane or argon, it is necessary to purge a part of it in order to prevent the concentration of such gases from building up too much in the gas passing over the catalyst. Since the purge gas is at only slightly under synthesis pressure, a useful energy recovery results from letting it down in an expansion engine. Since the purge gas is at the low temperature of methanol separation, it is capable of absorbing low-grade heat from other process streams in the plant and thus the energy recovery from purge gas is yet more valuable. After letting-down, the purge gas can be used as a fuel or source of hydrogen for purposes such as feedstock desulphurisation.

Such let-down of purge gas, especially after low-grade heat absorption, constitutes a second aspect of the invention, applicable also in methanol production processes outside the scope of the statement of the first aspect of the invention.

Although the first aspect of the invention resides essentially in transferring the heat evolved in methanol synthesis to water without boiling it, it is within the invention to conduct part of the synthesis so as to raise steam directly.

The first aspect of the invention is applicable to a methanol production process operated in conjunction with ammonia synthesis by making a nitrogen-containing crude synthesis gas and using the methanol synthesis purge gas as feed for the ammonia synthesis section.

Figure 2:
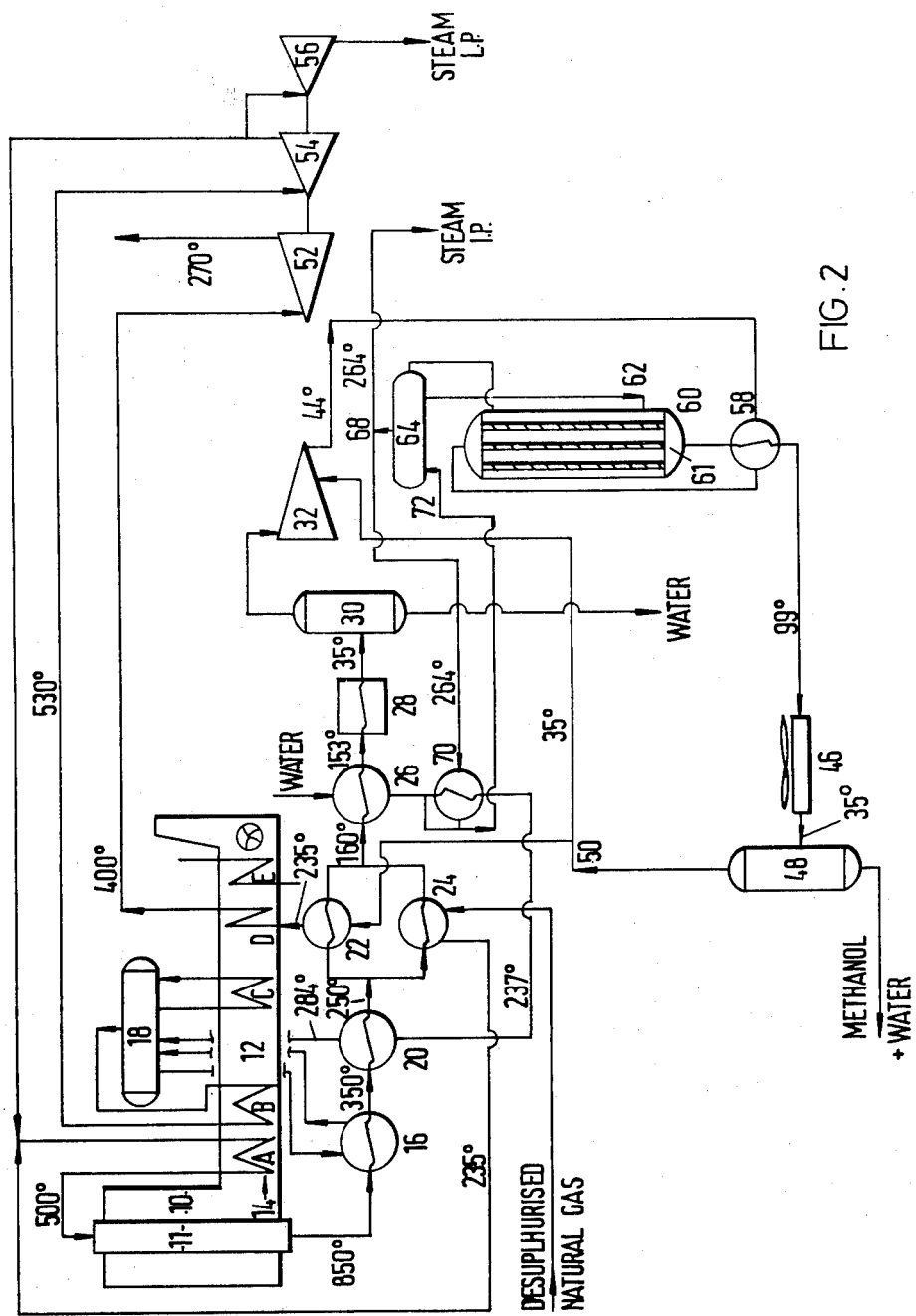

The drawings show two flowsheets of processes according to the invention:

FIG. 1 shows heat recovery from reacted synthesis gas directly as boiler feed water; and FIG. 2 shows generation of intermediate pressure steam in the synthesis reactor, followed by heating boiler feed water by condensation of such steam.

Both figures show power recovery by letting down synthesis purge gas through a turbine.

Synthesis gas generation section (common to both flowsheets).

Reformer 10 includes catalyst-filled tubes 11 suspended in a refractory lined box heated by burning natural gas (burners not shown) and having a flue gas duct 12 in which are disposed heat exchangers 14 A-E. Exchangers A-D will be referred to in relation to the streams to be heated in them. Exchanger E is a combustion air preheater for the natural gas burners. The feed to reformer 10 is a mixture of steam and desulphurised natural gas which has been preheated in exchanger 14A. (Desulphurisation is by known means and is not shown). Over the catalyst reaction occurs to give crude synthesis gas containing carbon oxides and hydrogen and excess steam. This gas is cooled in waste-heat boiler 16 and then in economiser 20, both of which with heat exchanger 14C, serve high-pressure steam drum 18. The gas is cooled further in parallel exchangers 22 and 24; in 22 it transfers heat to methanol synthesis purge gas and in 24 to natural gas to be mixed with steam. From these exchangers the gas passes to boiler feed water heater 26, cooler 28 (which may include a low-pressure boiler) and water-separator 30.

Methanol synthesis section as shown in FIG. 1

After separation of water at 30 the gas is compressed centrifugally by compressor 32 and mixed therein at an intermediate pressure level with recirculated gas from methanol separation. The mixed gas is divided at 33 into 2 streams, one of which is heated in exchangers 34 and 36 and fed to the main inlet 38 of synthesis reactor 40; and the other of which is fed without heating to the quench inlets 42 of reactor 40. (If desired, the gas stream can be divided between exchangers 34 and 36 and warmed gas fed to quench inlets 42). Quench inlets 42 suitably lead to spargers each disposed within a hollow bar having perforations small enough to prevent catalyst particles from entering but large enough to cause gas to pass from the catalyst bed into the bars so that it mixes with quench gas. Reacted gas heated by the exothermic synthesis reaction leaves reactor 40 and is divided at 42 into two streams, one of which passes through the hot side of exchanger 36 in which it heats incoming synthesis gas and the other of which passes through boiler feed water heater 44 in which it heats further the water that has been warmed in heater 26 and is to be passed via economiser 20 to high-pressure steam drum 18. The streams leaving exchanger 36 and heater 44 are re-united and passed through the hot side of exchanger 34 in which cold synthesis gas is warmed.

The gas is cooled to methanol condensation temperature in cooler 46. Methanol is recovered in separator 48. The unreacted gas leaving separator 48 is divided at 50 into a recirculation stream to be passed to the intermediate pressure section of compressor 32 and a purge stream to be treated for energy recovery by heating in exchangers 22 and 14D and letting down in turbine 52.

The power requirements of compressor 32 and the various other machines employed in carrying out the process are supplied by purge-gas let-down turbine 52, steam turbine 54 (high pressure pass-out) and steam turbine 56 (low pressure pass-out or condensing). Direct drives may be used or some or all of the turbines may generate electricity to be used in electric motor drives or, in favourable conditions to be exported.

Process example based on flowsheet of FIG. 1.

The heat recoveries in the process are illustrated by the stream temperatures (in degrees C) shown on the flowsheet. These relate to a process using 1600 kg mol/hour of natural gas as process feed and 91 metric tons/hour of steam at the inlet of reformer tube 11 and producing 41.665 metric tons/hour of methanol. The pressure at the exit of reformer tube 11 is 20 ata. and compression is to 102.3 ata at the inlet of reactor 40. The compositions and flow-rates of the gases in the synthesis section are as shown in Table 1.

The improvement in thermal efficiency resulting from the first aspect of the invention is based on the heat exchanged between reacted synthesis gas and boiler feed water in item 44, such that warm water (155° C) from exchanger 26 is heated to 237° C before being fed to the economisers 20 of the high pressure steam system. Since heating to 237° C is effected in the synthesis section, the sensible heat of the crude synthesis gas leaving economiser 20 is available for an intermediate level of heat recovery by exchange with purge gas at 22 and feed natural gas at 24. The improvement in thermal efficiency resulting from the second aspect of the invention is based on the let-down of purge gas from a pressure of 94 ata in turbine 52, after being the recipient of waste heat from synthesis gas in exchanger 22 and flue gas in exchanger 14D.

Methanol synthesis section as shown in FIG. 2

After separation of water at 30 the gas is compressed centrifugally at 32 and mixed in the compressor at an intermediate pressure level with recirculated gas from methanol separation. The mixed gas is heated in heat exchanger 58 to synthesis inlet temperature and fed to the inlet of synthesis reactor 60 in which it passes over methanol synthesis catalyst contained in tubes 61, which are surrounded by water. As the synthesis proceeds, heat is evolved and is absorbed by the water, which passes up into drum 64, where it boils, while liquid water is fed into the reactor shell at 62 to replace it. Reacted gas leaves reactor 60, passes through the hot side of heat exchanger 58 in which it gives up heat to cold gas from compressor 32, and is then cooled to methanol condensation temperature in cooler 46. Methanol is recovered in separator 48. The unreacted gas leaving separator 48 is divided at 50 into the recirculation stream to be passed to the intermediate pressure section of compressor 32 and a purge stream to be treated for energy recovery by heating in exchangers 22 and 14D and letting down in turbine 52. Steam generated in drum 64 is divided at 68 into two streams. One of these is passed to boiler feed water heater 70 in which condensation takes place in heat exchange with water that has been warmed in heater 26 and is to be passed via economiser 20 to high pressure steam drum 18. The other stream is exported. Part of the water warmed in heater 26 is fed with the condensed steam to drum 64 at 72.

The power requirements of compressor 32 and the various other machines employed in carrying out the process are supplied in the same way as for the process of FIG. 1.

Process example based on flowsheet of FIG. 2

The heat recoveries in the process are illustrated by the stream temperatures (in degrees C) shown on the flowsheet. Apart from the slightly lower temperature of the gas leaving item 26, the temperatures are the same as in FIG. 1, for the synthesis gas generation section. The compositions and flow rates of the process gases are the same as in the process of FIG. 1 and are set out in Table 1.

The improvement in thermal efficiency resulting in the process of FIG. 2 from the first aspect of the invention is based partly on the heat recovered as steam in reactor 60 and transferred to boiler feed water in item 70, such that warm water (155° C) from exchanger 26 is heated to 237° C before being fed to the economisers 20 of the high pressure steam system. As in the process of FIG. 1, the sensible heat of the crude synthesis gas leaving economiser 20 is available for an intermediate level of heat recovery by exchange with purge gas at 22 and feed natural gas at 24. The over-all thermal efficiency is rather better than that obtained using the process of FIG. 1 since the reacted gas entering the cooler is at 99° C instead of 120° C, so that less heat is discharged to atmosphere in cooler 46. The fuel consumption is, however, the same as in the process of FIG. 1, the greater efficiency being exploited in the form of exported intermediate pressure steam, as shown in Table 2.

TABLE 1

| Gas | Composition % v/v | | | | | | | Flow rate |
| | CO | $CO_2$ | $H_2$ | $CH_4$ | $H_2O$ | MeOH | $N_2$ | $Rm^3$/hour |
| --- | --- | --- | --- | --- | --- | --- | --- | --- |
| Fresh synthesis gas | 15.9 | 6.4 | 73.1 | 3.9 | 0.06 | — | 0.6 | 149800 |
| Reactor feed | 4.8 | 2.7 | 79.8 | 10.7 | 0.03 | 0.2 | 1.7 | 710040 |
| Reactor outlet | 1.7 | 1.6 | 76.5 | 11.8 | 1.4 | 5.1 | 1.9 | 646724 |
| Purge | 1.8 | 1.7 | 81.6 | 12.6 | 0.02 | 0.3 | 2.0 | 45424 |

The improvement in thermal efficiency due to the first aspect can be illustrated by considering the sources of the heat required to produce the high-pressure steam (145 metric tons/hour, 100 ata 530° C) from water at 110° C, as shown in Table 2. If the second aspect of the invention is used, as in the flow-sheet, a further $4.0 \times 10^6$ kg cal/hour are recovered.

TABLE 2

| | Quantity of heat, $10^6$ kg cal/hour | |
| Source of heat | Previous process | Invention process |
| --- | --- | --- |
| Cooling reformer gas from 850° C | 62.45 | 55.53 |
| Synthesis gas at 44 (directly or at 70 (via steam). | — | 12.68 |
| Reformer gas low-grade heat | — | 6.92 |
| Total recovered | 62.45 | 75.13 |
| Flue gas or extra fuel | 40.935 | 28.255 |
| Total required | 103.385 | 103.385 |
| Export steam, 50 ata | — | 8.050 |

TABLE 2-continued

| | Quantity of heat, $10^6$ kg cal/hour | |
| Source of heat | Previous process | Invention process |
| --- | --- | --- |
| (figure 2 only) | | |

Both aspects of the invention are applicable to processes in which methanol synthesis is combined with further reactions, such as the formation of dimethyl ether, hydrocarbons or oxygenated hydrocarbons.

I claim:

1. A methanol production process which comprises:
   a. generating methanol synthesis gas by reacting a carbonaceous feedstock with steam in one or more stages at the outlet of which there is delivered a gas stream at over 400° C;
   b. generating steam at a pressure of at least 50 ata by passing water in heat exchange with the gas stream of stage (a);
   c. bringing synthesis gas to synthesis pressure in the range 30 to 400 ata by means of a compressor driven by an engine in which such steam is let down;
   d. synthesizing methanol from synthesis gas by passing synthesis gas from stage (c) over a catalyst containing copper and zinc oxide at an outlet temperature of under 300° C;
   e. transferring heat evolved in the methanol synthesis of stage (d) from methanol-containing synthesis gas effluent to water to heat said water to a temperature in the range 200° C to 260° C, said water maintained under a pressure too high to permit boiling to take place, by passing said methanol-containing synthesis gas through two parallel heat exchangers, the first of which heats synthesis gas to methanol synthesis inlet temperature and the second of which heats said water;
   f. passing the hot water from stage (e) to stage (b) as a water source in the heat exchange for steam generation; and
   g. recovering methanol from the cooled methanol-containing synthesis gas from stage (e).

2. A process according to claim 1 in which the temperature of the gas stream after the heat exchange in stage (b) is more than 225° C.

3. A process according to claim 1 in which methanol synthesis gas is generated in stage (a) by a steam reforming process, said steam reforming process being fed by exhaust steam from the let-down engine of stage (c).

4. A process according to claim 3 including in stage (d) injecting cool synthesis gas into synthesis gas from (c) to control methanol synthesis temperature.

5. A methanol production process which comprises:
   a. generating methanol synthesis gas by reacting a carbonaceous feedstock with steam in one or more stages at the outlet of which there is delivered a gas stream at over 400° C;

b. generating steam at a pressure of at least 50 ata by passing water in heat exchange with the gas stream of stage (a);

c. bringing synthesis gas to synthesis pressure in the range 30 to 400 ata by means of a compressor driven by an engine in which such steam is let down;

d. synthesizing methanol from synthesis gas by passing synthesis gas from stage (c) over a catalyst containing copper and zinc oxide at an outlet temperature of under 300° C;

e. transferring heat evolved in the methanol synthesis of stage (d) to water maintained under a pressure that permits boiling, condensing the steam so produced in heat exchange with water to heat said water to a temperature in the range 200° to 260° C, said water maintained under a pressure too high to permit boiling to take place, and passing the methanol-containing synthesis gas effluent through a heat exchanger which heats synthesis gas to methanol synthesis inlet temperature;

f. passing the hot water from stage (e) to stage (b) as a water source in the heat exchange for steam generation; and g. recovering methanol from the cooled methanol-containing synthesis gas from stage (e).

6. A process according to claim 5 in which the temperature of the gas stream after the heat exchange in stage (b) is more than 225° C.

7. A process according to claim 5 in which methanol synthesis gas is generated in stage (a) by a steam reforming process, said steam reforming process being fed by exhaust steam from the let-down engine of stage (c).

8. A methanol production process which comprises:
a. generating methanol synthesis gas by reacting carbon monoxide with steam in one or more stages at the outlet of which there is delivered a gas stream at over 400° C;

b. generating steam at a pressure of at least 50 ata by passing water in heat exchange with the gas stream of stage (a);

c. bringing synthesis gas to synthesis pressure in the range 30 to 400 ata by means of a compressor driven by an engine in which such steam is let down;

d. synthesizing methanol from synthesis gas by passing synthesis gas from stage (c) over a catalyst containing copper and zinc oxide at an outlet temperature of under 300° C;

e. transferring heat evolved in the methanol synthesis of stage (d) from methanol-containing synthesis gas effluent to water to heat said water to a temperature in the range 200° C to 260° C, said water maintained under a pressure too high to permit boiling to take place by passing said methanol-containing synthesis gas through two parallel heat exchangers, the first of which heats synthesis gas to methanol synthesis inlet temperature and the second of which heats said water;

f. passing the hot water from stage (e) to stage (b) as a water source in the heat exchange for steam generation; and g. recovering methanol from the cooled methanol-containing synthesis gas from stage (e).

9. A process according to claim 8 in which the temperature of the gas stream after the heat exchange in stage (b) is more than 225° C.

10. A process according to claim 9 including in stage (d) injecting cool synthesis gas into synthesis gas from (c) to control methanol synthesis temperature.

11. A methanol production process which comprises:
a. generating methanol synthesis gas by reacting carbon monoxide with steam in one or more stages at the outlet of which there is delivered a gas stream at over 400° C;

b. generating steam at a pressure of at least 50 ata by passing water in heat exchange with the gas stream of stage (a);

c. bringing synthesis gas to synthesis pressure in the range 30 to 400 ata by means of a compressor driven by an engine in which such steam is let down;

d. synthesizing methanol from synthesis gas by passing synthesis gas from stage (c) over a catalyst containing copper and zinc oxide at an outlet temperature of under 300° C;

e. transferring heat evolved in the methanol synthesis of stage (d) to water maintained under a pressure that permits boiling, condensing the steam so produced in heat exchange with water to heat said water to a temperature in the range 200° to 260° C, said water maintained under a pressure too high to permit boiling to take place, and passing the methanol-containing synthesis gas effluent through a heat exchanger which heats synthesis gas to methanol synthesis inlet temperature;

f. passing the hot water from stage (e) to stage (b) as a water source in the heat exchange for steam generation; and g. recovering methanol from the cooled methanol-containing synthesis gas from stage (e).

12. A process according to claim 11 in which the temperature of the gas stream after the heat exchange in stage (b) is more than 225° C.

* * * * *